United States Patent
Gutman et al.

(10) Patent No.: US 6,538,138 B1
(45) Date of Patent: Mar. 25, 2003

(54) PROCESS AND A NOVEL INTERMEDIATE FOR THE PREPARATION OF FLECAINIDE

(75) Inventors: Arie L. Gutman, Haifa; Genady Nisnevich; Eleonora Shkolnik, both of Nesher; Igor Zaltzman, Haifa, all of (IL)

(73) Assignee: FineTech Ltd., Haifa (IL)

( * ) Notice: Subject to any disclaimer, the term of this patent is extended or adjusted under 35 U.S.C. 154(b) by 0 days.

(21) Appl. No.: 09/462,418

(22) PCT Filed: Jul. 7, 1998

(86) PCT No.: PCT/IL98/00315
§ 371 (c)(1),
(2), (4) Date: Apr. 3, 2000

(87) PCT Pub. No.: WO99/02498
PCT Pub. Date: Jan. 21, 1999

(30) Foreign Application Priority Data

Jul. 11, 1997 (IL) .................................................. 121288

(51) Int. Cl.[7] ...................... C07D 211/30; C07C 255/00
(52) U.S. Cl. ..................... 546/247; 558/399; 562/474; 560/65
(58) Field of Search ................................ 564/134, 161, 564/170; 560/8, 55, 62, 65; 514/328, 315, 316; 546/234, 244, 189, 247; 562/474; 558/399

(56) References Cited

U.S. PATENT DOCUMENTS 3,900,481 A * 8/1975 Banitt et al. ........... 260/293.77

FOREIGN PATENT DOCUMENTS

ES  2 007 802   7/1989
GB  2045760     11/1980

OTHER PUBLICATIONS

Shuichi Takayama et al, "Enzymatic resolutin of Amines and amino Alcohols Using Pent–4–enoyl Derivatives", Tet. Lett., vol. 37 (1996), pp. 6287–6290.*
Jefferson W. Tilley et al, "N–(Heterocyclic alkyl)pyrido[2,1–b]quinazoline–8carboxamides as Orally Acive antiallergy Agents", J. Med. Chem., vol. 30 (1987), pp. 185–193.*
Hitomi Suzuki et al, "Copper(I)–Assisted Synthesis of Aryl 2,3,4–Trifluoroethyl Ethers", Synthesis, (1985), pp. 499–500.*

Jay Wrobel et al, "Syntheses of Tolrestat Analogues Containing Additional Substituents in the Ring and Their Evaluation as Aldose Reductase Inhibitors.Identification of Potent, Orally Active 2–Fluoro Derivatives", J. Med. Chem., vol. 34(1991), pp. 2504–2520.*
Wrobel et al, "Syntheses of Tolrestat Analogues Containing Additional Substituents in the Ring and Their Evaluation as Aldose Reductase Inhibitors. Identification of Potent, Orally Active 2–Fluoro Derivatives", *J Med Chem* 34:2504–2520 (1991).
"Flecainide", *Merck Index*, 12th Edition, 4136, p. 694.
R. Buyle, "Sur les esters actives I. Aminolyse des derives acyles des oximes et amidoximes" *Helvetica Chimica Acta.*, vol. 47, pp. 2444–2448, (1964).

* cited by examiner

Primary Examiner—Paul J. Killos
(74) Attorney, Agent, or Firm—Needle & Rosenberg, P.C.

(57) ABSTRACT

The invention relates to processes for the preparation of compounds of the formula

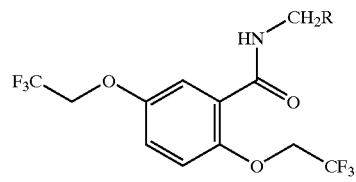

wherein R is a 2-piperidyl or 2-pyridyl radical, and pharmaceutically acceptable salts thereof, the process comprising the steps of:

a) reacting 2,5-bis(2,2,2-trifluoroethoxy)benzoic acid or a salt thereof with a haloacetonitrile to form a cyanomethyl ester of formula

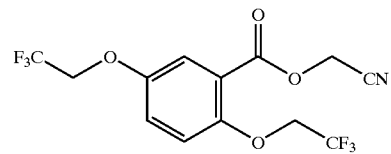

b) reacting the ester with an amine of the formula $RCH_2NH_2$, where R is as defined above.

12 Claims, No Drawings

PROCESS AND A NOVEL INTERMEDIATE FOR THE PREPARATION OF FLECAINIDE

FIELD OF THE INVENTION

This invention relates to a novel process for the preparation of Flecainide and a precursor thereof, to a novel intermediate used in this process and its preparation.

BACKGROUND OF THE INVENTION

Flecainide (2,5-bis(2,2,2-trifluoroethoxy)-N-(2-piperidylmethyl)benzamide is an effective antiarrythmic drug that acts on the cell membrane to reduce fast inward depolarization current.

One prior art method for preparing Flecainide, disclosed inter alia, in British Patent Application No. 2,045,760 A, starts from 2,5-bis(2,2,2-trifluoroethoxy)benzoic acid. This starting material is prepared by a multi-stage process, comprising the conversion of 1,4-dibromobenzene or hydroquinone to 1,4-bis(2,2,2-trifluoroethoxy)benzene, which is acetylated to form 2,5-bis(2,2,2-trifluoroethoxy) acetophenone. The acetophenone is then oxidized to form the corresponding benzoic acid derivative, which is then converted to its acid chloride and reacted either with 2-(aminomethyl)piperidine to form the Flecainide product in one step or with 2-(aminomethyl)pyridine, followed by catalytic hydrogenation of the pyridine ring, to form the Flecainide product in two steps.

The one step process has a serious disadvantage in that the acid chloride reacts non-selectively with both nitrogen atoms of the 2-(aminomethyl)piperidine, resulting in a mixture of the two acylated isomers. This is the main reason why the two-step process via the pyridine intermediate is commercially preferred. A further disadvantage is due to the fact that the acid chloride intermediate disclosed in GB 2,045,760A is a liquid which can not be stored for long periods of time but must be used immediately after it is prepared.

OBJECTS OF THE INVENTION

It is an object of this invention to provide a novel process for the preparation of Flecainide and its pharmaceutically acceptable salts, which is free of the above-mentioned disadvantages, starting with commercially available halobenzoic acids and involving the use of simple reagents and low cost solvents, to afford high overall yield of the Flecainide product.

It is a further object of this invention to provide a novel reactive intermediate, i.e. the cyanomethyl ester of 2,5-bis (2,2,2-trifluoroethoxy)benzoic acid, which is capable of reacting selectively with the primary amino group of 2-(aminomethyl)piperidine, so as to form the Flecainide product in high yield and free of the above mentioned isomeric by-product.

SUMMARY OF THE INVENTION

The above objects are achieved in accordance with the present invention which, in one aspect thereof, provides a process for preparing a compound of formula (A):

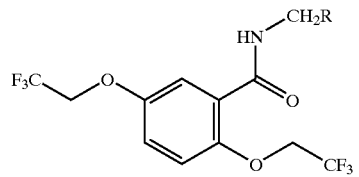
(A)

wherein R is a 2-piperidyl or 2-pyridyl radical, and pharmaceutically acceptable salts thereof, which process comprises the steps of:

a) reacting 2,5-bis(2,2,2-trifluoroethoxy)benzoic acid or a salt thereof, with a haloacetonitrile of the formula XCH₂CN, where X is Cl, Br or I, if necessary in the presence of an inorganic or organic base, to form the cyanomethyl ester of the formula (II):

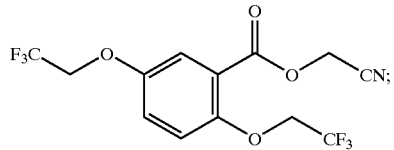
(II)

b) reacting the ester of the formula (II) with an amine of the formula RCH₂NH₂, where R is as defined above and, if desired, c) converting the compound of the formula (A) to a pharmaceutically acceptable salt thereof.

In accordance with another aspect of this invention, there is provided the novel cyanomethyl ester of 2,5-bis(2,2,2-trifluoroethoxy)benzoic acid having the formula (II) above. As contrasted to the liquid acid chloride intermediate disclosed in GB 2,045,760A, the novel intermediate of the present invention is a stable, solid compound, obtainable in high yield, which can be easily purified by cristallisation and stored for long periods of time.

DETAILED DESCRIPTION OF THE INVENTION

It was shown by Schwizer et al. (Helvetica Chimica Acta, 1955, V.38,69;80;83) that cyanomethyl esters of aliphatic amino acids react selectively with primary amino groups, R. Buyle (Helvetic Chimica Acta, 1964, V. 47, 2444) showed, that benzylamine reacts with cyanomethyl benzoate considerably slower than with cyanomethyl acectate. The present invention is based on the unexpected finding that 2,5-bis(2, 2,2-trifluoroethoxy)benzoic acid activated by conversion to its cyanomethyl ester may react selectively and with high yield with primary amino groups of amines of the formula RCH2NH2, wherein R is as defined above.

Accordingly, the cyanomethyl ester (II) is prepared in high yield, starting with 2,5-bis(2,2,2-trifluoroethoxy) benzoic acid which is reacted with a haloacetonitrile of the formula XCH₂CN wherein X is Cl, Br or I, preferably Cl, in the presence of an inorganic or organic base. Alternatively, the ester (II) can be prepared by reacting a salt of 2,5-bis (2,2,2-trifluoroethoxy)benzoic acid with a haloacetonitrile.

Suitable organic bases for use in the above process are primarily tertiary amines, e.g. triethylamine, diisopropylethylamine, ethylpiperidine and the like, preferably triethylamine. Inorganic bases which may also be used are, e.g., alkali metal or alkaline earth metal carbonates or bicarbonates.

In the second step of the process, the cyanomethyl ester (II) is reacted with an amine of the formula $RCH_2NH_2$, where R is as defined above, optionally in a suitable, inert solvent. Thus, the reaction may be carried out by mixing together 2-(aminomethyl)piperidine with the ester (II) in a solvent such as 1,2-dimethoxyethane or ethyl acetate, or yield Flecainide (I) in a high yield.

The optional conversion of Flecainide into a pharmaceutically acceptable salt such as the acetate salt, is carried out by conventional methods.

The starting material 2,5-bis(2,2,2-trifluoroethoxy) benzoic acid is preferably prepared by the process described in co-pending Israel Application No. 120715. Accordingly, this benzoic acid derivative is prepared by contacting a halobenzoic acid of the formula (III):

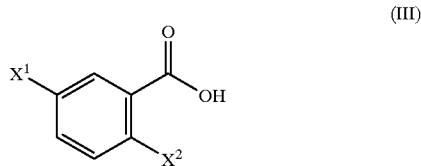

or a salt thereof, wherein $X^1$ is selected from Br or I, and $X^2$ is selected from Cl, Br or I, or one of $X^1$ and $X^2$ may also be $CF_3CH_2O—$, with 2,2,2-trifluoroethanol in the presence of a strong base and copper iodide and/or copper bromide, in an aprotic solvent. Suitable solvents are dipolar aprotic solvents or N-containing heterocycles or their mixtures, such as N,N-dimethylformamide, 1-methyl-2-pyrrolidinone, N,N-dimethylacetamide, DMSO, pyridine, picolines, lutidines, collidines, methylethylpyridine (MEP), quinoline and substituted quinolines. As the strong base there may be used Na, NaH, $NaNH_2$, Na— and K-alcoholates, NaOH, KOH and the like, most preferably NaH. For example, 5-bromo-2-chlorobenzoic acid is reacted while heating, with 2,2,2-trifluoroethanol and a strong base, e.g. sodium hydride in a dipolar aprotic solvent, e.g. N,N-dimethylformamide, in the presence of copper iodide.

The present invention will be described in more detail with the aid of the following non-limiting examples.

EXAMPLE 1

Synthesis of 2,5-bis(2,2,2-trifluoroethoxy)benzoic acid

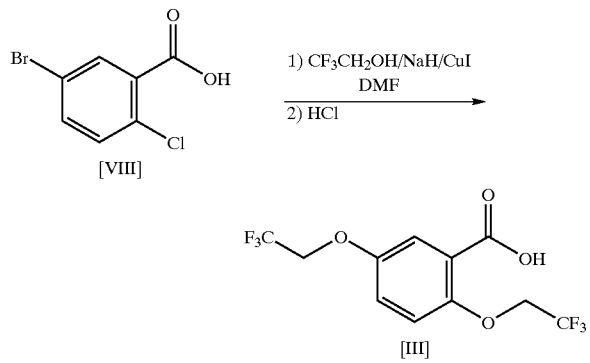

A 1 L round-bottomed flask equipped with a magnetic stirrer, a thermometer pocket, dropping funnel and a reflux condenser, was charged with 51.0 g of a 60% strength suspension of sodium hydride in mineral oil (equivalent to a total of 30.6 g (1.28 mole) of pure NaH) and 570 mL of anhydrous N,N-dimethylformamide. The mixture was cooled to room temperature in an ice-water bath and 189.5 g (1.90 mole) of anhydrous 2,2,2-trifluoroethanol were added dropwise during 40 minutes.

The mixture was cooled to room temperature and 24.8 g (0.13 mole) of anhydrous copper iodide and 59.5 g (0.25 mole) of 5-bromo-2-chlorobenzoic acid were added. The black reaction mixture was heated to about 110–115° C. and kept at this temperature for 2 hours.

The reaction mixture was cooled to room temperature and poured into a mixture of crushed ice (3 kg) and conc. hydrochloric acid (0.78 L). The mixture was vigorously stirred for 1 hour, the black precipitate was filtered off and washed at once with 200 mL of water. The obtained solid was suspended at room temperature in 1 L of 5% aqueous KOH under vigorous stirring for 15 min, followed by filtration through a Celite modified filter and washing with 100 mL of 5% aqueous KOH.

The transparent clear alkaline solution was thrice extracted with 150 mL of dichloromethane. The alkaline solution was added dropwise under vigorous stirring to mixture of 0.6 kg of ice and 0.2 L of conc. hydrochloric acid, at a temperature not higher than 0° C. and a pH 1. The mixture was stirred for 0.5 hours at these conditions. The obtained precipitate was filtered off, washed with water, collected and dried under vacuum to a constant weight. Yield: 64.7 g (81.4%) of crude 2,5-bis(2,2,2-trifluoroethoxy) benzoic acid, m.p. 116–118° C. After recrystallisaiton from an ethanol/water system, a product with m.p. 120–121° C. was obtained.

EXAMPLE 2

Synthesis of cyanomethyl ester of 2,5-bis(2,2,2-trifluoroethoxy)benzoic acid

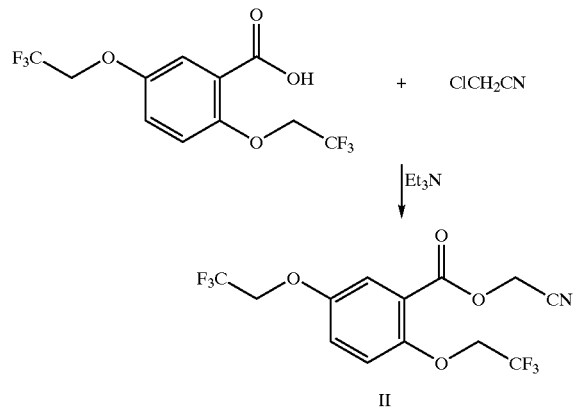

A 1 L two-neck round-bottomed flask equipped with a heating mantle, a magnetic stirrer and a reflux condenser was charged under argon with a mixture of 62.8 g (197.4 mmole) of 2,5-bis(2,2,2-trifluoroethoxy)benzoic acid, 22.4 g (296.1 mmole) of chloroacetonitrile and 29.9 g (296.1 mmole) of triethylamine in 250 mL ethyl acetate (EtOAc). The obtained mixture was refluxed for 3 hours. After cooling to 10° C., the mixture was filtered through a column containing 50 g of silica gel to remove the formed triethylammonium chloride. The filtrate was evaporated in vacuo and the product was dried under high vacuum for 1 hour at 50° C. The resulting colourless solidified oil was stirred with 200 mL of cold hexane to obtain white crystals. The crystals were filtered off, washed with cold hexane and dried at reduced pressure to give 60.0 g (85% yield) of cyanomethyl ester (II), having a purity of 99.5% (GC), m.p. 50–51° C., one spot on TLC. $^1$H NMR ($CDCl_3$) δ 4.37 (4H, m); 4.93

(2H, s); 7.00 (1H, d); 7.17 (1H, dd); 7.44 (1H, d); HRMS:M+ 357.0433, $C_{13}H_9NO_4F_6$.

EXAMPLE 3
Synthesis of Flecainide (I) from the cyanomethyl ester of 2,5-bis(2,2,2-trifluoroethoxy)benzoic acid (II) and 2-(aminomethyl)piperidine

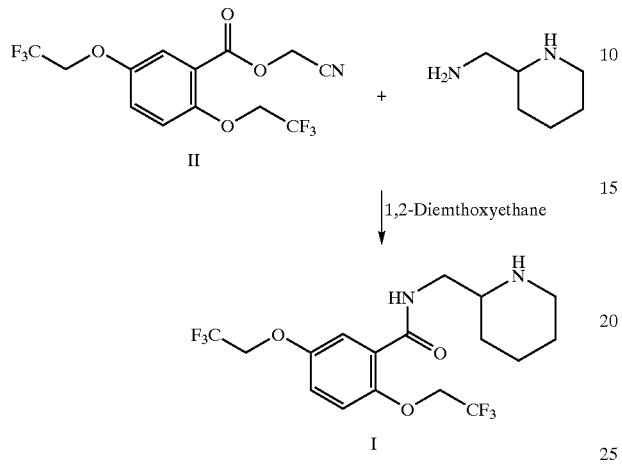

A mixture of compound (II) (2.1 g, 5.9 mmole) and 2-(aminomethyl)piperidine (0.8 g, 7 mmole) in 1,2-dimethoxyethane (10 mL) was charged under argon into a 50 mL round-bottomed flask equipped with a magnetic stirrer. After stirring for 2.5 hours at room temperature, additional 2-(aminomethyl)piperidine (0.5 g, 4.7 mmole) was aded. The mixture stirred for additional 24 hours at room temperature. The solvent was removed in vacuo and the residue was dissolved in 10 mL methylene chloride. The obtained solution was extracted with water and the aqueous layer was extracted with additional 5 mL of methylene chloride. The combined organic layers were dried over sodium sulphate and evaporated under reduced pressure to give 1.9 g (77.6% yield) of white crystals of Flecainide (I), purity 99.1% (GC).

EXAMPLE 4
Synthesis of Flecainide Acetate (IV)

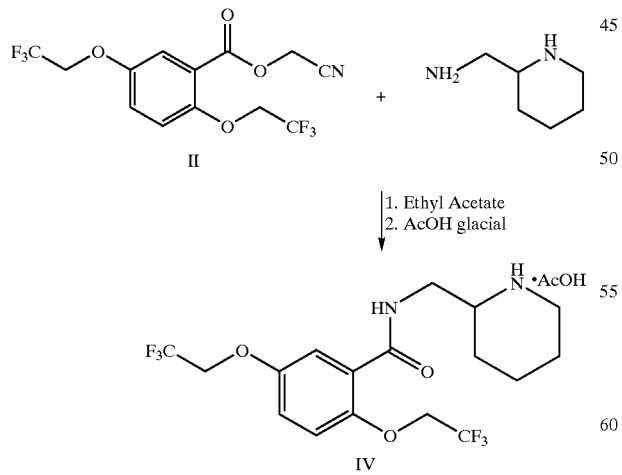

A mixture of compound (II) (95.0 g, 0.27 mole) and 2-(aminomethyl)piperidine (35.4 g, 0.31 mole) in 450 mL ethyl acetate (max water content: 0.05%) was charged under argon into a 1 L round-bottomed flask equipped with a dropping funnel and magnetic stirrer. After stirring for 2 hours at room temperature, the additional amount (24.2 g, 0.21 mole) of 2-(aminomethyl)piperidine was added and the mixture was stirred for an additional period of 12 hours at room temperature. The solvent was evaporated under reduced pressure. The residue was dissolved in 250 mL of dichloromethane. The obtained solution was treated with water (3×50 mL) dried with anhydrous $Na_2SO_4$, filtered and concentrated under reduced pressure.

The residue was dissolved in boiling ethyl acetate (800 mL), 30 g (0.5 mole) of glacial acetic acid was added dropwise to the obtained solution. The mixture was stirred under reflux for an additional 10 minutes and allowed to cool to room temperature overnight followed by cooling into an ice bath for 4 hours. The crystalline product was filtered off, washed with cooled to 0° C. ethyl acetate (2×100 mL) and dried at 50° C. under reduced pressure, to obtain 103.0 g (82% from theoretical yield) of Flecainide acetate, m.p. 147–148° C.

EXAMPLE 5
Synthesis of 2,5-bis(2,2,2-trifluoroethoxy)-N-(2-pyridylmethyl)-benzamide (V)

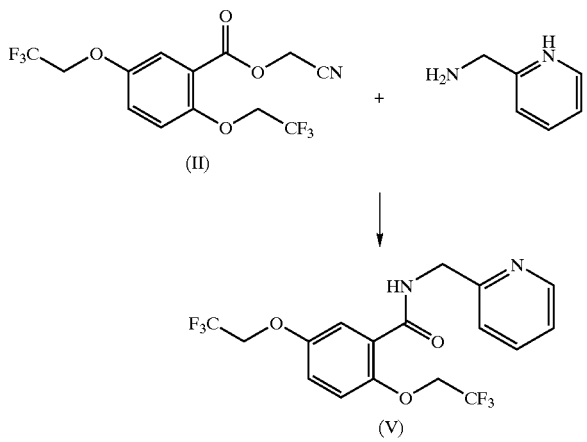

To a solution of 8.93 g (2.5 mmole) of compound (II) in 80 mL of ethyl acetate under argon, 2-(aminomethyl)pyridine (3.2 g, 3.0 mmole) were added with stirring and the mixture was refluxed for 4 hours. An additional 1 g of 2-(aminomethyl)pyridine was added and the mixture was refluxed for two more hours. The ethyl acetate was evaporated under reduced pressure and the residue was passed through a 12 cm column containing silica gel with a mixture of methylene chloride:hexane (1:1) as eluent. The column was washed with methylene chloride and the combined solutions were evaporated under reduced pressure. The residue was crystallized from $CH_2Cl_2$:hexane (1:2) to give 7 g (69% yield) of 2,5-bix(2,2,2-trifluoroethoxy)-N-(2-pyridylmethyl)benzamide (V) m.p. 104–106° C., purity 99.8% (GC).

What is claimed is:
1. A process for the preparation of a compound of formula (A):

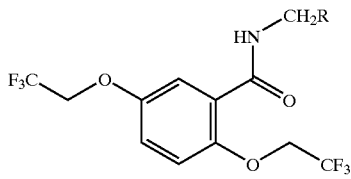
(A)

wherein R is a 2-piperidyl or 2-pyridyl radical, and pharmaceutically acceptable salts thereof, which process comprises the steps of:
  a) reacting 2,5-bis(2,2,2-trifluoroethoxy)benzoic acid or a salt thereof, with a haloacetonitrile of the formula $XCH_2CN$, where X is Cl, Br or I, if necessary in the presence of an inorganic or organic base, to form the cyanomethyl ester of the formula (II):

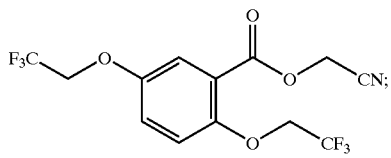
(II)

b) reacting the ester of the formula (II) with an amine of the formula $RCH_2NH_2$, where R is as defined above and, if desired,
  c) converting the compound of the formula (A) to a pharmaceutically acceptable salt thereof.

2. A process according to claim 1, wherein the reactions in steps a) and/or b) and/or c) are carried out in a suitable inert solvent.

3. A process according to claim 2, wherein ethyl acetate is used as the solvent in steps a) and/or b), and/or c).

4. A process according to claim 1, wherein the free 2,5-bis(2,2,2-trifluoroethoxy)benzoic acid is used as the starting material is step a) and the reaction is conducted in the presence of a base.

5. A process according to claim 4 wherein a tertiary amine is used in step a) as a base.

6. A process according to claim 5, wherein the tertiary amine is selected from triethylamine, diisopropylethylamine, ethylpiperidine.

7. A process according to claim 1, wherein R is 2-piperidyl to obtain Flecainide (I).

8. A process according to claim 7 further comprising the conversion of the Flecainide product to its acetate is step c) of claim 1.

9. Cyanomethyl ester of 2,5-bis(2,2,2-trifluoroethoxy)benzoic acid of the formula (II) in claim 1.

10. A process for the preparation of the cyanomethyl ester of the formula (II) in claim 1, which comprises reacting 2,5-bis(2,2,2-trifluoroethoxy)benzoic acid or a salt thereof, with a haloacetonitrile of the formula $XCH_2CN$ wherein X is as defined in claim 1 and, if necessary, in the presence of an inorganic or organic base.

11. A process according to claim 10, carried out in a suitable inert solvent.

12. A process according to claim 10, wherein 2,5-bis(2,2,2-trifluoroethoxy)benzoic acid is prepared by contacting a halobenzoic acid of the formula (III):

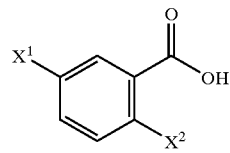
(III)

or a salt thereof, wherein $X^1$ is selected from Br or I, and $X^2$ is selected from Cl, Br or I, or one of $X^1$ and $X^2$ may also be $CF_3CH_2O-$, with 2,2,2-trifluoroethanol in the presence of a strong base and copper iodide and/or copper bromide, in an aprotic solvent.

* * * * *

UNITED STATES PATENT AND TRADEMARK OFFICE
CERTIFICATE OF CORRECTION

PATENT NO. : 6,538,138 B1
DATED : March 25, 2003
INVENTOR(S) : Gutman et al.

It is certified that error appears in the above-identified patent and that said Letters Patent is hereby corrected as shown below:

<u>Title page,</u>
Item [56], References Cited, OTHER PUBLICATIONS, insert the following:

-- Zurita et al., "Preparation of 2,5-bis(2,2,2-trifluoroethoxy-N-(2-piperidinylmethyl) benzamide acetate," Bibliographic Information, Answer:1.
Derwent Information, Abstract of JP 05039240.
Banitt et al., "Antiarrhythmics. N-(Aminoalkylene) trifluoroethoxybenzamides and N-(Aminoalkylene) trifluoroethoxybenzamides," Journal of Medicine of Chemistry, vol. 18, no. 11, pp. 1130-1134 (1975).
Banitt et al., "Antiarrhythmics. 2. Synthesis and Antiarrhythmic Activity of N-(Piperidylalkyl) trifluoroethoxybenzamides," Journal of Medicine of Chemistry, vol. 20, no. 6, pp. 821-826 (1977).
Schwyzer et al., "Uber aktivierte Ester. II. Synthese aktivierter Ester von Aminosaure-Derivaten," Helvetica Chimica Acta., vol. 38, no. 9, pp. 80-91 (1955).
Schwyzer et al., "Uber aktivierte Ester. I. Aktivierte Ester der Hippursaure und ihre Umsetzungen mit Benzylamin," Helvetica Chimica Acta., vol. 38, no. 7-8, pp. 69-79 (1955).
Schwyzer et al., "Uber aktivierte Ester. III. Umsetzungen Aktivierter Ester von Aminosaure- und Peptide-Derivaten mit Aminen und Aminosaureestern," vol. 38, no. 9-10, pp. 83-91 (1955). --

Signed and Sealed this

Seventeenth Day of February, 2004

JON W. DUDAS
*Acting Director of the United States Patent and Trademark Office*